(12) United States Patent
Maurer et al.

(10) Patent No.: US 7,731,958 B2
(45) Date of Patent: Jun. 8, 2010

(54) USE OF BROMELAIN FOR THE TREATMENT OF INFLAMMATORY DISEASES AND FOR ADJUVANT THERAPY DURING WOUND HEALING PROCESSES

(75) Inventors: Rainer Maurer, Berlin (DE); Klaus Eschmann, Kleinblittersdorf (DE)

(73) Assignee: Ursapharm Arzneimittel GmbH & Co. KG, Saarbrucken (DE)

( * ) Notice: Subject to any disclaimer, the term of this patent is extended or adjusted under 35 U.S.C. 154(b) by 810 days.

(21) Appl. No.: 10/399,926

(22) PCT Filed: Nov. 28, 2001

(86) PCT No.: PCT/EP01/13897

§ 371 (c)(1),
(2), (4) Date: Apr. 24, 2003

(87) PCT Pub. No.: WO02/43755

PCT Pub. Date: Jun. 6, 2002

(65) Prior Publication Data

US 2004/0043018 A1        Mar. 4, 2004

(30) Foreign Application Priority Data

Nov. 28, 2000   (EP)   .................................. 00125986

(51) Int. Cl.
    *A61K 38/46*       (2006.01)
(52) U.S. Cl. .................................. 424/94.65
(58) Field of Classification Search ........................ None
    See application file for complete search history.

(56) References Cited

U.S. PATENT DOCUMENTS 3,224,942 A * 12/1965 Martin ..................... 424/94.65
5,560,910 A * 10/1996 Crandall .................. 424/94.63

FOREIGN PATENT DOCUMENTS

EP          0 421 021 A1    10/1991
WO          WO 96/00082      4/1996

OTHER PUBLICATIONS

Pirotta F et al. Bromelain- a deeper pharmacological study. Note I. Antiinflammatory and serum fibrinolytic activity after oral administration in the rat, Drugs under Experimental and Clinical Research, 1978, 4(1): 1-20.*
Nickoloff B.J. & Nestle F.O. Recent insights into the immunopathogenesis of psoriasis provide new therapeutic opportunities, The Journal of Clinical Investigation, Jun. 2004, 113(12): 1664-1675, entire document.*
Nickoloff B.J. et al, The cytokine and chemokine network in psoriasis, Clinics in Dermatology, 2007, 25: 568-573, entire document.*
Donahue K.E. et al, Systematic review: comparative effectiveness and harms of disease-modifying medications for rheumatoid arthritis, Annals of Internal Medicine (epub. ahead of publication, Nov. 19, 2007): projected publication—Jan. 15, 2008, 148(2): 1-11 and W1, entire document.*
Gillissen A. Managing asthma in the real world, Int. J. Clin. Pract., Jun. 2004, 58(6): 592-603, entire document.*
Van kampen V. et al, Occupational allergied to bromelain, Pneumologie, Mar. 2007, 61(3): 159-161, English abstract.*
Thornhill S M et al. "Natural treatment of perennial allergic treatment" Alternative Medicine Review, 2000, vol. 5, pp. 448-454.*
Alam R et al. "Agonistic-Antagonistic Property of Interleukin 8 on Basophils Identification of IL-8 As a Potent Inhibitor of Cytokine-Induced Histamine Release" Journal of Allergy and Clinical Immunology, 1991, vol. 87, No. 1 Part 2, p. 241 (Abstract).*
Taussig et al. article entitled "Bromelain, the enzyme complex of pineapple (*ananas comosus*) and its clinical application. An update" *Journal of Ethnopharmacology*, 22 (1988) pp. 191-203.
Thornhill et al. article entitled "Natural Treatment of Perennial Allergic Rhinitis" *Alternative Medicine Review*, vol. 5, No. 5, pp. 448-454.
Alam et al. abstract entitled "Agonistic-antagonistic property of interleukin 8 on basophils: Identification of IL-8 as a potent inhibitor of cytokine-induced histamine release" XP-001002229, p. 241.

* cited by examiner

*Primary Examiner*—Jon P Weber
*Assistant Examiner*—Satyendra K Singh
(74) *Attorney, Agent, or Firm*—K&L Gates LLP

(57) ABSTRACT

The present application pertains to the use of bromelain preparing a medicament for increasing the IL-(8) level in an individual so as to reduce or prevent inflammation in said individual and as an adjuvant therapy during wound healing processes.

11 Claims, 1 Drawing Sheet

USE OF BROMELAIN FOR THE TREATMENT OF INFLAMMATORY DISEASES AND FOR ADJUVANT THERAPY DURING WOUND HEALING PROCESSES

BACKGROUND OF THE INVENTION

The present invention relates to the use of bromelain and components thereof for the manufacture of a medicament for increasing the IL-8 level in an individual so as to reduce or prevent inflammatory diseases in said individual and to use it as an adjuvant therapy to promote wound healing processes.

Inflammation, or the inflammatory process, respectively involves several biological reactions, proceeding in three successive phases: the degenerative phase, the vascular phase, and the healing phase.

In the degenerative phase, the affected cells become swollen. The cytoplasma of affected cells becomes vacuolized and an enlargement and fragmentation of cell nuclei can be observed. As some of the platelets in the damaged blood vessels disintegrate, mediators acting on sympathetic nerve endings are released.

Subsequently, in the vascular phase changes in the blood vessels can be observed. In particular, an extensive migration and activity of so-called inflammatory cells (granulocytes, particularly neutrophils, lymphocytes, macrophages and monocytes) and clearing of cellular debris and degenerated cells occur during this phase. As the capillary network and the postcapillary venules become flooded, congested and engorged by blood in active hyperemia and as a number of capillaries proliferate, a reddish appearance of inflamed tissue results.

In the last phase, the healing phase, the inflammation begins to subside and repair of wound starts.

Often inflammatory processes result in the formation of oedema, an accumulation of liquid in inter-tissue spaces, as the transport activity with respect to osmotic active compounds is locally decreased in the inflamed areas. Closely related to this phenomenon are swellings observed after operations or traumata, often causing considerable pain to the patient.

On a molecular basis, a plethora of active mediators are involved in the development of inflammation, such as e.g. cytokines and in particular interleukin 1-α, interleukin 1-β, interleukin 6, tumor necrosis factor α and β, interleukin 8 (IL-8).

In particular, IL-8 has been found to attract granulocytes and neutrophils towards an inflamed area and to activate the functional capacities of granulocytes, such as phagocytosis, cytotoxicity, chemotaxis etc. IL-8 is a non-glycosylated protein of 8 kDa having 72 amino acids and is also known as ANAP (anionic neutrophil activating peptide), GCP (granulocyte chemotactic peptide), LCF (lymphocyte chemotactic factor) and LIF (leukocyte inhibitory factor). IL-8 is produced in various cells e.g. monocytes/macrophages, granulocytes, T-cells, fibroblasts or endothelium cells as response to proinflammatory stimuli, such as IL-1, TNF, LPS and viruses.

Conventionally, the treatment of inflammatory conditions and oedema utilized an oral administration of non-steroidal anti-inflammatory drugs (NSAIDS), such as e.g. acetylsalicylic acid, phenylbutazone, diclofenac or indometacine. However, these agents exhibit several, sometimes severe secondary effects, e.g. gastrointestinal problems and adverse effects on gastro-enteric mucosa.

To overcome these drawbacks the art provided additional agents for treating inflammation. In this respect the WO 98/13057 discloses the use of a composition containing a Tripterygium wilfordii Hook F root preparation that has anti-inflammatory properties. Yet, since this composition also exhibits immunosuppressive activity the effect thereof in treating inflammation was rather poor. Further, in EP 100 94 04 the use of pADPRT (poly-ADP ribose polymerase) inhibitory compounds are proposed for the treatment of inflammatory diseases. However, also in this case unwanted secondary effects occur upon administration.

Therefore, there is a need in art for additional, well tolerated agents for treating inflammatory diseases and/or inflammatory diseases that do not show unwanted side effects.

SUMMARY OF THE INVENTION

Consequently, according to a first aspect the present invention provides the use of bromelain or one or more components thereof for the manufacture of a medicament for increasing the IL-8 level in an individual.

Bromelain, an extract from pineapple stem (*Ananas comosus*), is a mixture of various compounds, such as enzymes, e.g. proteases, phosphatases, peroxidases, cellulases, protease inhibitors etc., carbohydrates and other not yet identified components. Pharmacological studies relating to bromelaine showed that only in very rare cases allergic reactions were observed. Moreover, these reactions normally wear off relatively quickly.

During the extensive studies leading to the present invention, it was now surprisingly found that administration of bromelain to patients reduced the onset and length of inflammatory diseases, and also improved the conditions during wound healing processes. Since bromelain as a food ingredient is well accepted by the body only minimal or no side effects are observed. This anti-inflammatory effect of bromelain is obviously mainly due to increasing the IL-8 secretion by cells of the immune system, which IL-8 secretion stimulates immune responses in an area of inflammation and attracts immune cells to said area by the process of chemotaxis. As a result of such a stimulation the immune processes involved in inflammatory processes may actually perform a quicker and more efficient task at the location of inflammation so that the actual physiological conditions experienced by an individual suffering from an inflammatory condition are less severe and are reduced more quickly.

According to the invention a variety of different disease states may be treated that are based on inflammatory responses, such as psoriasis, rheumatoid arthritis, polyarthritis. Moreover, since the action of bromelain in reducing inflammation in an individual is based on an stimulation of the individual's own immune system, said compound may well be utilized for an adjuvant therapy during wound healing processes and allergy.

On the other hand IL-8 is known to inhibit histamine release from basophil and mast cells and therefore antagonizes the IL-4 induced production of IgE by B-lymphozytes. Consequently, bromelain or components thereof is suitable as an anti-allergic agent, in particular as an antihistaminikum.

The one or more of the components of bromleain is/are preferably non-protease component(s) thereof, since the stimulating activity of bromelain is even retained when bromelain has been subjected to high temperature treatment that Additional features and advantages of the present invention are described in, and will be apparent from, the detailed description of the presently preferred embodiments and the drawings.

BRIEF DESCRIPTION OF THE DRAWINGS

The invention will now be further described with reference to the following examples and to the drawing, wherein.

DETAILED DESCRIPTION OF THE INVENTION

Figure 1:
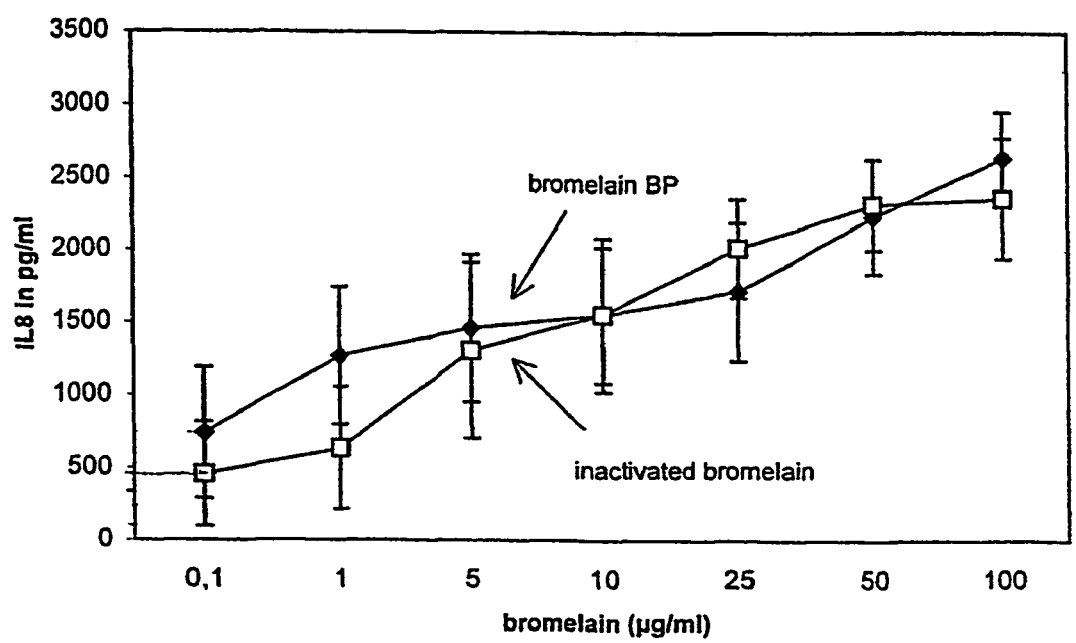
FIG. 1 shows the effects of bromelain BP (bromelain base powder) and heat inactivated bromelain on the secretion of IL-8 from neutrophils of healthy donors. Three independent experiments were performed.

The present invention provides for the use of bromelain or one or more compounds thereof for the manufacture of medicament for increasing the IL-8 level in an individual. In addition, the present invention provides a medicament including bromelain.

By way of example and not limitation, examples of the invention will now be given.

Example

Effects of Bromelain BP and of Heat Inactivated Bromelain on the Secretion of IL-8 from Neutrophils Bromelain Base Powder (BP)

Bromelain BP (purchased from CPC Wolfgang Mühbauer GmbH, Hamburg, Germany) was dissolved in water and lyophilised. Proteolytic activity and protein content were determined by using the substrate L-Pyr-Phe-Leu-pNA (Harrach et al., J Protein Chem 14 (1995) 41-52) and the Bio-Rad Protein Assay (Bio-Rad Laboratories GmbH, Munchen, Germany), respectively. Bromelain BP showed a specific activity of 0.34 U/mg. The protease activity was destroyed by heating the bromelain BP solution at 80° C. for 1 h.

Preparation of Neutrophils

Neutrophils were isolated by a single-step method as described by Ferrante et al. (J. Immunol. Methods. 36 (1980) 109).

About 20-30 ml of freshly isolated blood donated by a healthy volunteer was anticoagulated with preservative free heparin (10 U/ml final concentration, Sigma, Deisenhofen, Germany) and layered onto Polyrnorphprep (Nycomed Pharma, Oslo, Norway). After centrifugation (400 g, 30 min) at 20° C. the neutrophils were harvested from the second leukocyte band. One ml of water was added for 1 min to the cell suspension to lyse the erythrocytes. Cells were washed three times with PBS. Cell viability, determined by trypan blue exclusion, was found to be greater than 98%.

Secretion of IL-8:

IL-8 was quantitated in cell-free supernatants using a sandwich enzyme immunoassay technique (R&D Systems, Minneapolis, USA). $2\times10^5$ neutrophils were incubated at 37° C. with or without test substance in microtiterplates having 96 wells. 24 hours incubation cells were centrifuged (400×g, 7 min) and cell free supernatants were used. Samples and standards were pipetted into the IL-8 monoclonal antibody pre-coated wells and incubated 2.5 hours at room temperature. Then the cells were washed and the substrate solution was added. The colour development was stopped and determined using a microtiterplate reader (SLT Labinstruments, Austria).

Statistical Analysis:

Statistical significance between treatment and control groups was calculated using the Mann-Whitney-Wilcoxon test and the computer programme Instat.

Experimental Results:

Bromelain BP and heat inactivated bromelain were tested for their capability to increase the secretion of IL-8 in neutrophils.

Neutrophils were incubated with various amounts of bromelain BP and heat treated bromelain BP (range of 0.1 µg/ml-100 µg bromelain BP) for a total of 24 hours. As can be seen in FIG. 1 bromelain BP and heat treated bromelain BP induced a significant increase in the secretion of IL-8 into the supernatant in a dose dependent manner, in the range of about 450 pg/ml-2640 pg/ml IL-8. Neutrophils not activated with bromelain BP and heat inactivated bromelain did not show any IL-8 secreted into the supernatant.

Since also heat treated bromelain base powder was able to stimulate IL-8 secretion it may be concluded that the proteolytic activity does not correlate with the ability for neutrophil activation.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for increasing the IL-8 level in an individual comprising the step of administering to an individual a composition comprising heat-treated bromelain.

2. The method of claim 1 wherein functional capacities of granulocytes are stimulated.

3. The method of claim 1, wherein an effective amount of the composition is administered for the treatment of inflammatory diseases.

4. The method of claim 1, wherein an effective amount of the composition is administered as adjuvant therapy during wound healing processes.

5. The method of claim 3, wherein the inflammatory disease is associated with psoriasis, rheumatoid arthritis, polyarthritis or allergy.

6. The method of claim 5, wherein the composition is an anti-histaminic agent.

7. The method of claim 1, wherein the heat-treated bromelain comprises a component of bromelain, the component comprising an inactivated protease activity.

8. A method for the treatment of inflammatory diseases, the method comprising administering to an individual having an inflammatory disease a medicament including a heat-treated bromelain at a therapeutically effective level to increase the IL-8 level in the individual, wherein the heat-treated bromelain comprises a component of bromelain, the component comprising an inactivated protease activity.

9. The method of claim 8, wherein the medicament is designed for adjuvant therapy during wound healing processes.

10. The method of claim 8, wherein the inflammatory disease is associated with psoriasis, rheumatoid arthritis, polyarthritis or allergy.

11. The method of claim 10, wherein the medicament is an anti-histaminic agent.

* * * * *